(12) United States Patent
Krueger et al.

(10) Patent No.: US 6,478,751 B1
(45) Date of Patent: *Nov. 12, 2002

(54) BONE MARROW ASPIRATION NEEDLE

(75) Inventors: John A. Krueger, Milwaukee, WI (US); Greg Groenke, Gurnee, IL (US); Grant A. Clark, Bristol, WI (US); Edward Sherman, Valrico, FL (US)

(73) Assignee: Allegiance Corporation, McGaw Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/552,481

(22) Filed: Apr. 18, 2000

(51) Int. Cl.⁷ .................................................. A61B 5/00
(52) U.S. Cl. ........................................................ 600/566
(58) Field of Search ........................ 600/562, 564–567, 600/573, 576, 578; 606/167, 170; 604/22, 35, 44

(56) References Cited

U.S. PATENT DOCUMENTS

| | | | | |
|---|---|---|---|---|
| 2,919,692 A | * | 1/1960 | Ackermann | 600/567 |
| 3,661,144 A | * | 5/1972 | Jensen et al. | 604/22 |
| 4,598,710 A | * | 7/1986 | Kleinberg et al. | 600/564 |
| 5,111,828 A | * | 5/1992 | Kornberg et al. | 600/567 |

* cited by examiner

Primary Examiner—Max Hindenburg
(74) Attorney, Agent, or Firm—Andrew G. Rozycki; Donald O. Nickey (57) ABSTRACT

The present invention provides an aspiration device that includes an outer cannula 16, a stylet 14, and an aspiration needle 80. The aspiration needle includes hollow cannula 82 and an aperture 93. The outer cannula 16 defines a distal tip 29 that is tapered to provide a distal cutting edge. The stylet 14 is designed to be inserted in the outer cannula 16. The stylet 14 also defines a sharp distal tip 30. The hollow cannula 82 designed to be inserted in the outer cannula 16. A distal end 91 of the hollow cannula 82 is closed and an aperture 93 is defined in a side of the hollow cannula 82.

37 Claims, 9 Drawing Sheets

BONE MARROW ASPIRATION NEEDLE

TECHNICAL FIELD OF THE INVENTION

The present invention relates to medical instruments utilized in aspirating liquid samples from bone structures.

BACKGROUND OF THE INVENTION

A biopsy medical instrument is an instrument which is designed to take samples of tissue. Typically, a biopsy device that is utilized to obtain samples from the bone consists of a hollow cannula that is surrounding a stylet. The stylet includes a sharp distal tip which extends outwardly from the cannula when the stylet is secured inside the cannula. The combined cannula and stylet is used to penetrate through the outer layer of the bone, called the cortex, which is considerably harder than the trabecular bone layer and the tissue within the bone that is sampled, referred to as the marrow. Once the stylet and cannula have penetrated the cortex, the stylet is removed and the cannula is extended further into the medular cavity, thereby capturing marrow tissue for a sample.

The architecture of the tissue sample that is removed by the biopsy device is critical in several respects. Initially, the size of the sample is important, with larger tissue sample sizes representing better samples for subsequent testing to be performed on the tissue. However, the larger the cannula and stylet that are inserted into the bone, the more pain is generated at the site of the penetration for the patient. In addition, it is important that the sample be taken without damaging the marrow tissue. However, in removing the tissue sample the tissue must be excised from the remaining tissue. This removal can result in compromising the tissue sample by damaging the tissue sample.

Several approaches have been taken to secure large, undamaged tissue samples using bone marrow biopsy devices. However, each of these approaches has significant drawbacks which limit commercial and clinical usefulness. For example, one such approach utilizes suction provided at the proximal end of the cannula. The suction is designed to pull the tissue sample into the cannula and retain the tissue sample inside the cannula. While in theory such suction would help secure larger tissue samples, in practice exposure to such suction forces results in damage to the marrow tissue when the sample is removed from the patient.

Another approach utilizes a snare in the form of a coil at the distal end of the cannula. When rotated, the coil decreases in diameter to secure the biopsy tissue sample in the cannula. While again in theory such a device would help secure larger tissue samples, in practice it subjects the tissue sample to compression forces which causes damage to the sample.

Other approaches include the use of inwardly projecting members such as scallops within the cannula. The theory behind such devices is that when the tissue sample is captured by the cannula, the inward direction of the scallops allows the tissue sample to slide over such projecting members but when the tissue sample is removed from the patient the projecting members latch onto the tissue sample to secure the tissue sample in the cannula. Again, however, this theory fails in practice as it causes trauma to the tissue when the tissue sample is removed from the patient.

Other approaches include providing apertures on the side of the cannula which, in theory, allow tissue to expand into such apertures to help secure the tissue sample in the cannula. Likewise, one approach utilizes a screw member in the cannula which is designed to urge the tissue inwardly and retain the tissue sample in of the cannula. Once again, providing a cavity for the tissue sample that is not smooth results in damage to the tissue when the tissue sample is removed from the patient.

Yet another approach at securing the biopsy sample within the cannula involves the use of a pair of coaxial cannulas. One of the two cannulas includes a curved section that acts as a cam to compress the inner cannula around the tissue sample when the inner cannula is withdrawn from the outer cannula. Once again, in theory this would help to secure the tissue within the cannula, but in practice it subjects the tissue sample to such compression forces that damage to the sample is caused. In addition, the use of dual cannulas acts to either decrease the size of the tissue sample or to increase the size of the biopsy device causing increased pain to the patient. A similar approach utilizes an additional coaxial hollow cannula designed to sheer or cut-off the tissue when the two cannulas are rotated relative to each other. However, because such devices require additional hardware in the cannula, either the size of the tissue sample is decreased or the size of the biopsy device is increased.

In addition, it is often clinically useful to aspirate the bone marrow to obtain marrow liquid for additional testing. With devices of the prior art, an outer cannula and a stylet of a biopsy needle is used to gain access to the medular cavity through the cortex of the bone. The stylet is removed and suction is applied in order to pull the marrow liquid out of the marrow tissue.

Because of the trauma such aspiration causes to the marrow tissue due to thrombotic cascading, considerable destruction to the marrow tissue occurs at the site of the aspiration. Thus, in the prior art a tissue sample taken through the same access site as the aspiration would be adulterated. Therefor, a tissue sample is typically taken from an access site separate from the aspiration site. Two separate access sites result in increased pain to the patient and increased possibility of infection.

What would be desirable is an aspiration device that is able to aspirate a sample while minimizing the pain experienced by the patient during such procedure. Such a device would also avoid subjecting the patient to an increased risk of infection.

SUMMARY OF THE INVENTION

The present invention provides an aspiration device that is able to aspirate a sample while minimizing the pain experienced by the patient during such procedure. The present invention further avoids subjecting the patient to an increased risk of infection. The present invention provides an aspiration device that includes an outer cannula, a stylet and a hollow cannula with an aperture. The outer cannula defines a distal tip that is tapered to provide a distal cutting edge. The stylet is designed to be inserted in the outer cannula. The stylet also defines a sharp distal tip. The hollow cannula is designed to be inserted in the outer cannula. The distal end of the hollow cannula is closed and an aperture is defined in a side of the hollow cannula.

Thus, there is disclosed an aspiration device comprising: an outer cannula secured in a handle, the outer cannula defining a distal tip that provides a distal cutting edge; a stylet designed to be inserted in the outer cannula, the stylet defining a sharp distal tip; a hollow cannula designed to be inserted in the outer cannula; and an aperture defined in a side of the hollow cannula.

Thus, there is further disclosed an aspiration device comprising: a housing; a hollow cannula secured in the housing, a distal end of the hollow cannula being closed; and an aperture defined in a side of the hollow cannula.

There is further disclosed an aspiration device comprising: an outer cannula secured in a handle; a stylet designed to be inserted in the outer cannula; and a hollow cannula designed to be inserted in the outer cannula, the hollow cannula adapted to define an aspiration zone generally to the side of the hollow cannula.

There is disclosed a kit for administering an aspiration comprising: an outer cannula secured in a handle, the outer cannula defining a distal tip that provides a distal cutting edge; a stylet designed to be inserted in the outer cannula, the stylet defining a sharp distal tip; a hollow cannula designed to be inserted in the outer cannula; and an aperture defined in a side of the hollow cannula.

There is disclosed a method for aspirating bone marrow tissue comprising: inserting a stylet into an outer cannula; penetrating the bone cortex with the stylet and the outer cannula to enter the medular cavity; removing the stylet; inserting an aspiration needle into the outer cannula; creating a suction through the aspiration needle; removing the aspiration needle; further inserting the outer cannula into the medular cavity, thereby trapping bone marrow tissue within the outer cannula; and removing the bone marrow tissue from the patient.

DETAILED DESCRIPTION OF A PREFERRED EMBODIMENT

Figure 1:
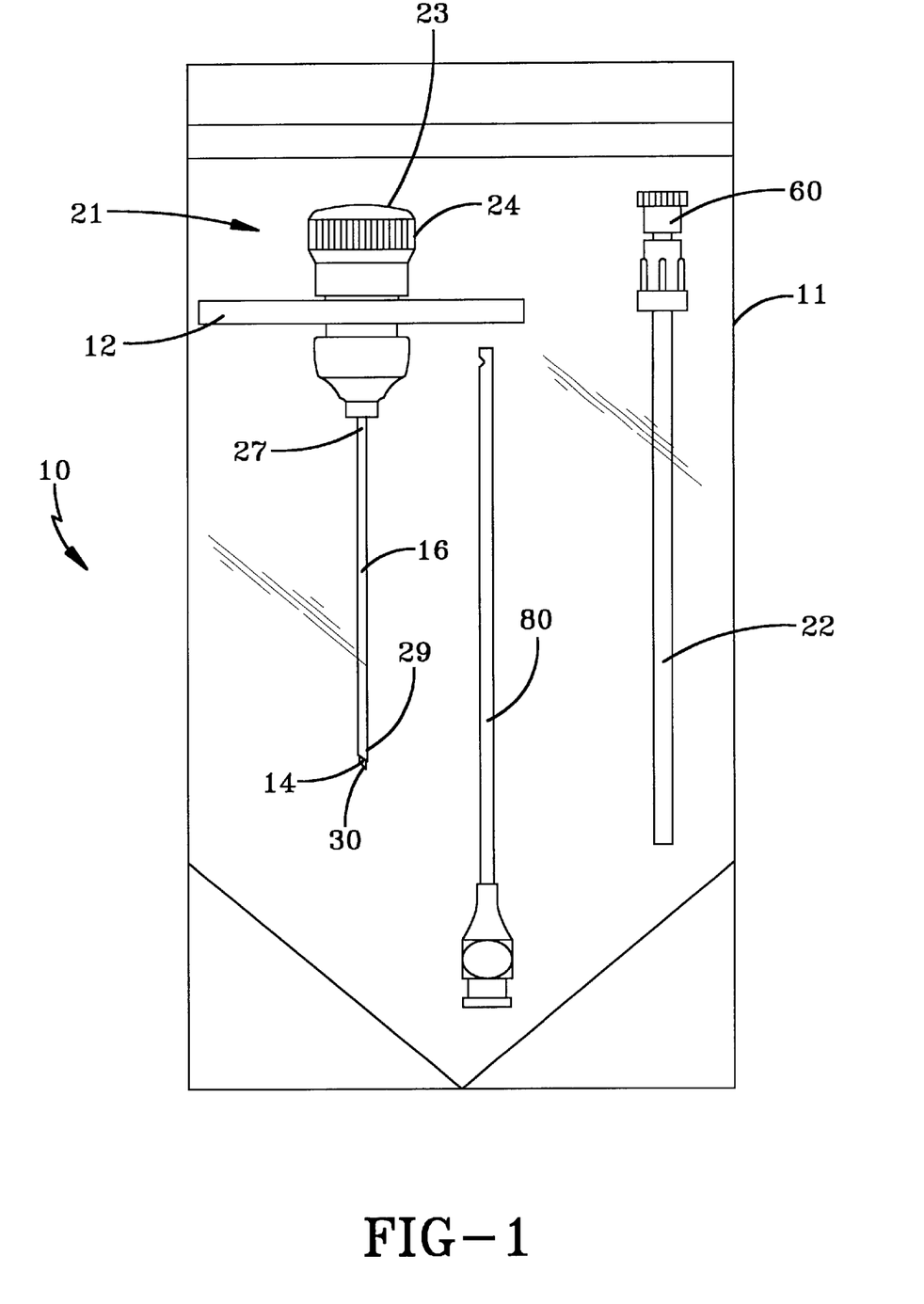
FIG. 1 is an elevational view of an outer cannula and an inner cannula in accordance with the principles of the present invention in the form of a kit packaged in a container.

Referring first to FIG. 1, a bone marrow biopsy device made in accordance with the principles of the present invention in a package is generally designated by the reference number 10. A bone marrow biopsy device 10 made in accordance with the principles of the present invention includes a handle 12, a stylet 14, an outer cannula 16, an inner member 18, an ejector pin 20, and a protective sheath 22. The bone marrow biopsy device 10 made in accordance with the principles of the present invention is preferably provided to the user sterile in a package 11.

Because the bone marrow biopsy device 10 made in accordance with the principles of the present invention must be inserted through the hard outer cortex layer of a bone, the handle 12 is designed to ergonomically nest in the palm of a health care professional. Thus, a proximal portion 21 of the handle 12 includes a tapered cap 23 designed to fit into the middle portion of the palm. The tapered cap 23 is adapted to engaged to the handle 12. In a preferred embodiment, the tapered cap 23 is threadingly engaged to cooperating threads on the handle 12. In addition, the tapered cap 23 may include a scored outer surface top 24 to assist the health care professional is securing and removing the cap 23.

The handle 12 is designed so that the outer cannula 16 extends between the index and the middle finger of the health care professional. This allows the health care professional to exert a great deal of pressure on the handle 12 from the palm of the hand. This further allows the health care professional to direct the device 10 into the patient utilizing the fingers that are wrapped around the handle 12. In a preferred embodiment, the handle 12 is molded from a hard plastic.

The bone marrow biopsy device 10 made in accordance with the principles of the present invention includes an outer cannula 16. The outer cannula 16 is permanently secured at a proximal end 27 to the handle 12. The distal tip 29 of the outer cannula 16 is tapered to provide a distal cutting edge, best seen in FIG. 2A. The outer cannula 16 is preferably designed of a hard material to withstand the forces applied on the outer cannula 16 when penetrating through the cortex of the bone. Thus, in a preferred embodiment the outer cannula 16 is made of stainless steel.

Figure 2A:
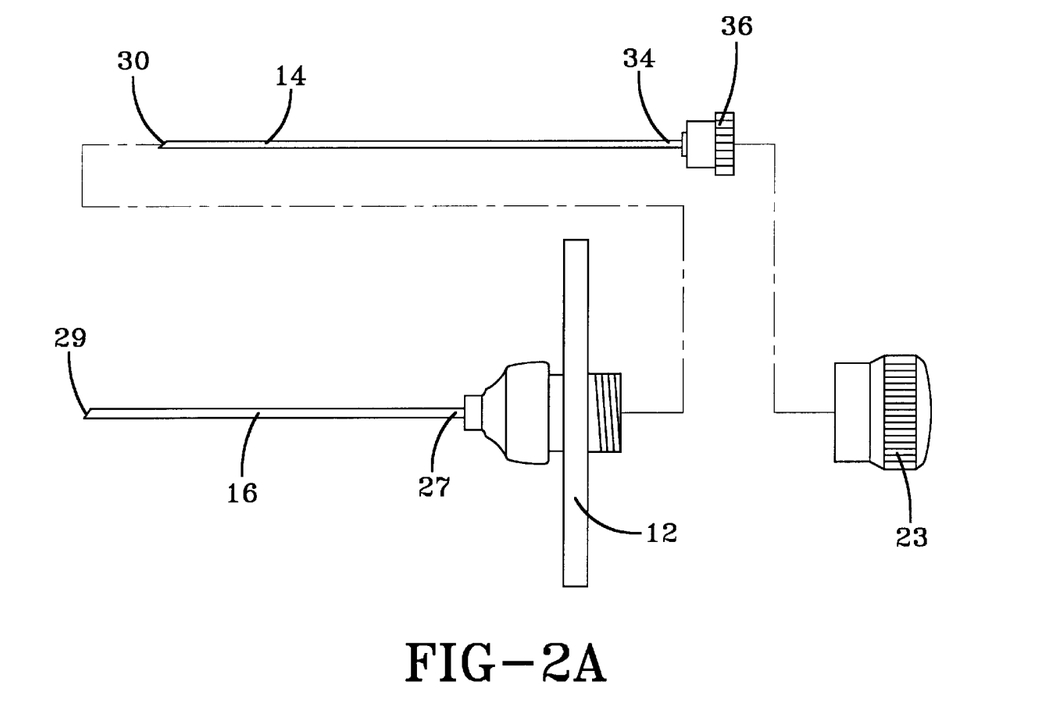
FIG. 2A is a perspective, exploded view of the handle including the outer cannula, the cap and the stylet of the bone marrow biopsy device of FIG. 1.

The bone marrow biopsy device 10 made in accordance with the principles of the present invention also includes a stylet 14, best seen in FIG. 2A. The stylet 14 includes a sharp distal tip 30 designed to penetrate the hard cortex layer of a bone. Like the outer cannula 16, the stylet 14 is preferably designed of a hard material to withstand the forces applied on the stylet 14 when penetrating through the cortex of the bone, such as stainless steel.

A proximal end 34 of the stylet 14 includes a stylet retaining housing 36. The stylet retaining housing 36 is designed to secure the stylet 14 within the handle 12. Thus, the stylet retaining housing 36 is adapted to be contained within the ergonomic design of the cap 23. In addition, the stylet retaining housing 36 is retained within the handle 12 so that the stylet 14 cannot rotate while penetrating the bone cortex. In a preferred embodiment, the stylet retaining housing 36 is relatively square and is secured in a cooperating relatively square receiving cavity (not shown) within the handle 12.

The stylet 14 is adapted to be secured within the outer cannula 16 in order to penetrate the bone cortex. Thus, the outer diameter of the stylet 14 is slightly smaller than the inner diameter of the outer cannula 16. When the stylet 14 is inserted into the outer cannula 16 and the stylet retaining housing 36 is secured in the handle 12, the sharp distal tip 30 of the stylet 14 extends slightly beyond the distal tip 29 of the outer cannula 16, as seen in FIG. 1. Thus, the sharp distal tip 30 of the stylet 14 works in conjunction with the sharp distal tip 29 of the outer cannula 16 to assist in penetrating the bone cortex.

Figure 2B:
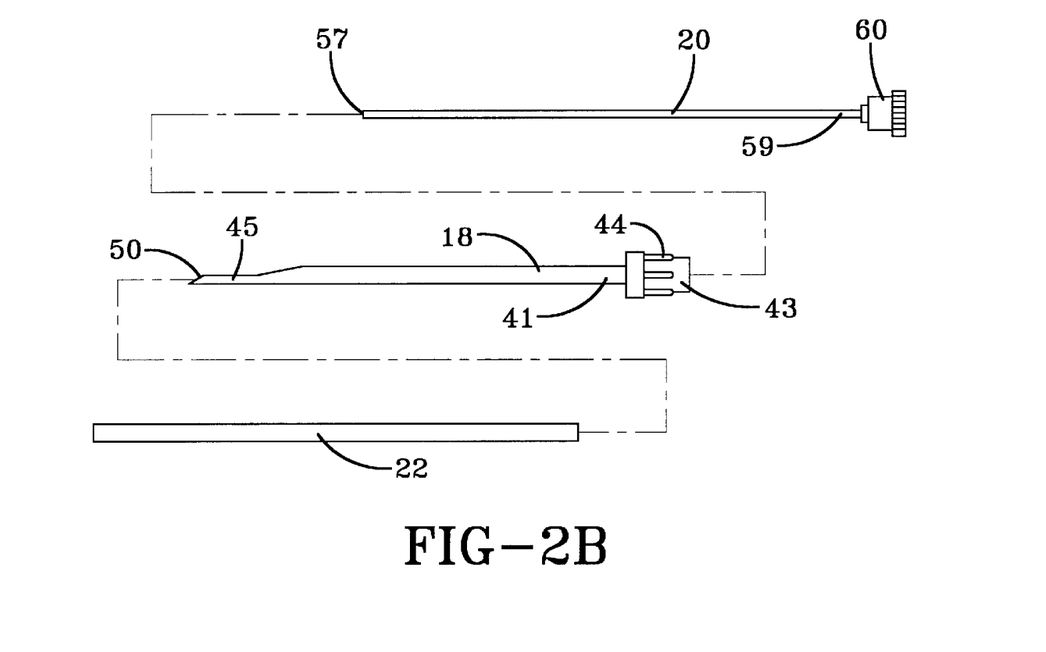
FIG. 2B is a perspective, exploded view of the inner member, the ejector pin, and the protective sheath of the bone marrow biopsy device of FIG. 1.

Referring now to FIG. 2B, the bone marrow biopsy device 10 made in accordance with the principles of the present invention also includes an inner member 18. A proximal end 41 of the inner member 18 is formed with a hub 43 that is secured to the inner member 18. The hub 43 includes a plurality of ribs 44 to aid in rotation of the hub 43 during use. A distal end of the inner member 18 defines a cutting finger 45. The width of the cutting finger 45 is preferably designed such that the cutting finger 45 is wide enough to maintain the structural integrity of the cutting finger 45 while being sufficiently narrow to avoid subjecting the tissue sample to compression forces.

Figure 3A:
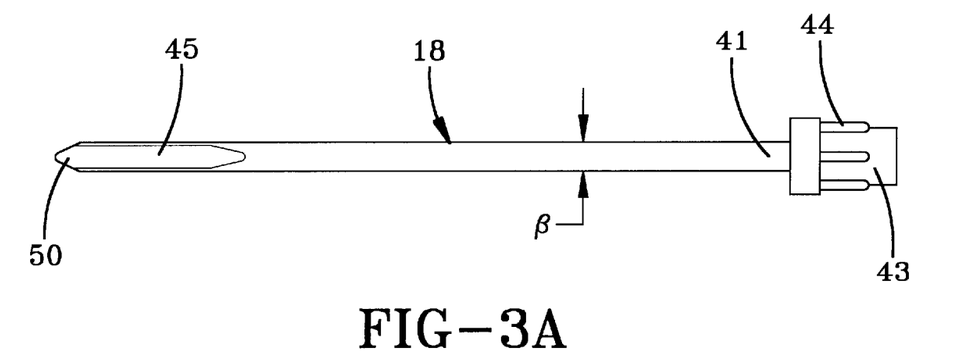
FIG. 3A is a close-up top view of the inner member showing the cutting finger of FIG. 2B.
Figure 3B:
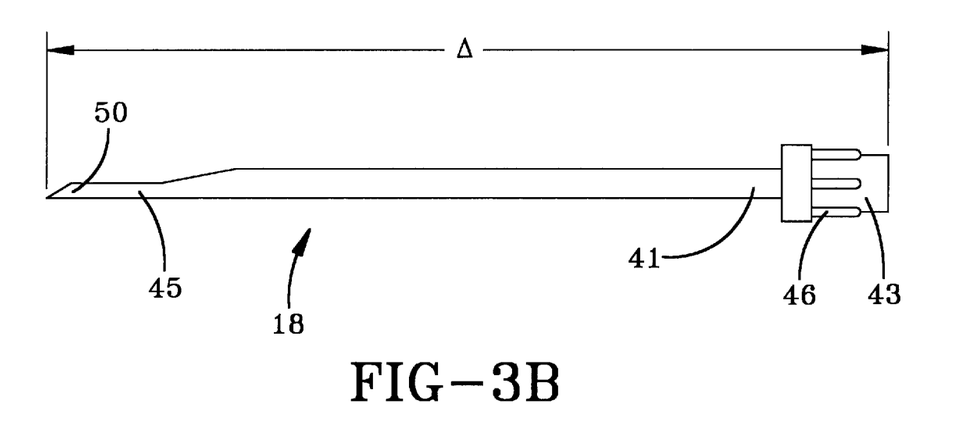
FIG. 3B is a close-up side view of the inner member showing the cutting finger of FIG. 2B.
Figure 4:
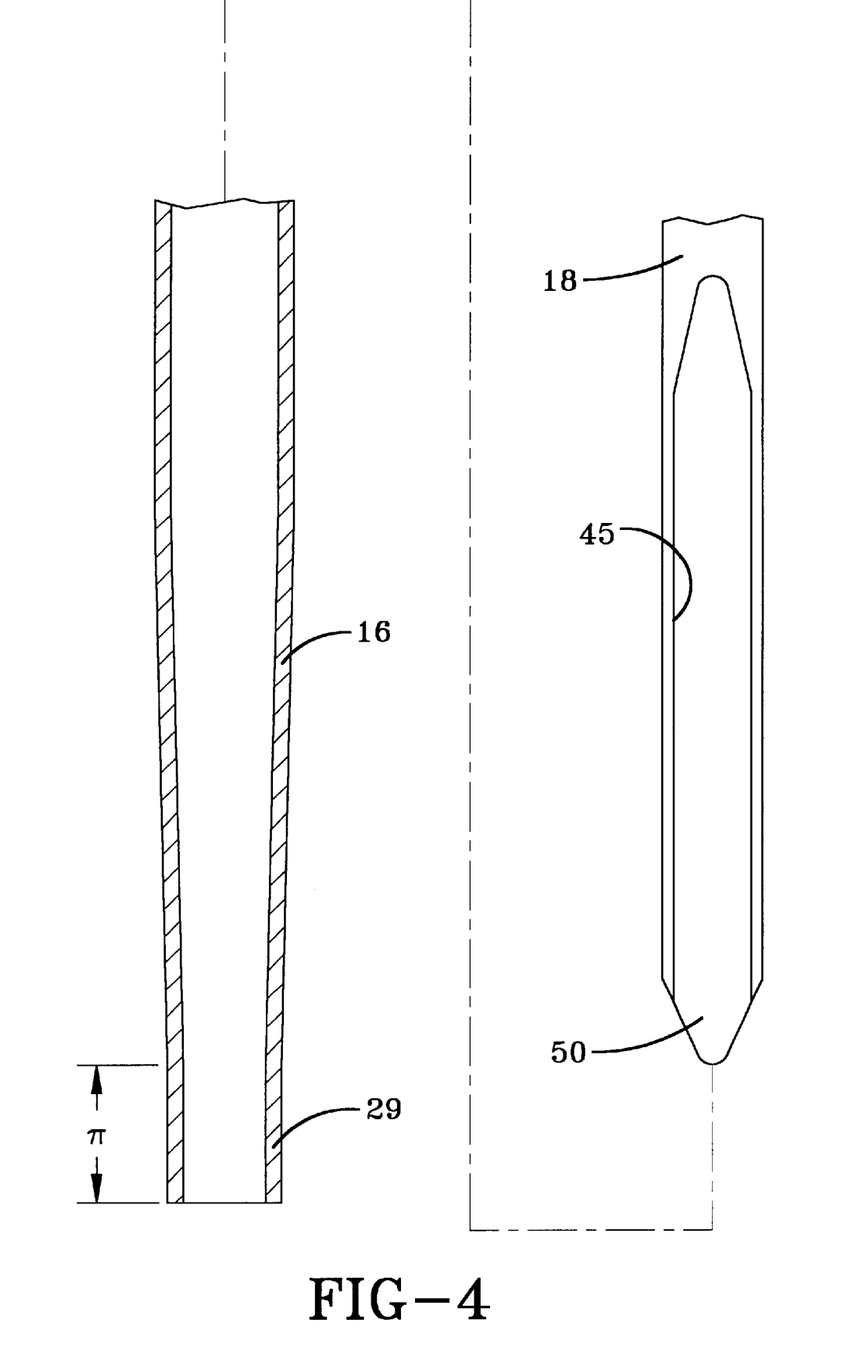
FIG. 4 is a close-up top view of the cutting finger of FIG. 3 and cross-sectional view of the outer cannula of FIG. 2.

Referring now to FIGS. 3 and 4, close-ups of the cutting finger 45 are seen. In a preferred embodiment, the width of the cutting finger 45 is approximately 60% of the circumference of the inner member 18. By cutting finger 45, it is met in an embodiment a blade-type member having generally sharp edges that is capable of cutting the tissue sample substantially from the bone marrow tissue without subjecting the tissue sample to undue compression forces and while being capable of structurally withstanding the force exerted on the blade. It has been found that if the cutting finger 45 is equal to or greater than about 60% of the circumference of the inner member 18, then the tissue sample is subjected to undue compression forces, thus causing undue tissue damage.

In one embodiment, the cutting finger is formed by grinding about at least 40% of the circumference of the inner member 18 away thereby forming a blade-type member having generally sharp edges. In addition, a distal tip 50 of the cutting finger 45 is beveled to facilitate cutting of the tissue sample. The taper of the distal tip 29 (seen in FIG. 2A) of the outer cannula 16 directs the cutting finger 45 inwardly. The inward extension of the cutting finger 45 causes the cutting finger 45 to sever the tissue sample from the tissue.

As seen in FIG. 2B, the bone marrow biopsy device 10 made in accordance with the principles of the present invention further includes an ejector pin 20. The ejector pin 20 is a solid piece designed to fit within the inner diameter of the inner member 18. A distal end 57 of the ejector pin 20 is blunt to avoid damaging the tissue sample when it is removed from the inner member 18. A proximal end 59 of the ejector pin 20 includes an ejector pin housing 60. The ejector pin housing 60 is designed to secure the ejector pin 20 within the inner member 18.

Finally, the bone marrow biopsy device 10 made in accordance with the principles of the present invention includes a protective sheath 22. The protective sheath 22 is designed to surround the inner member to protect the cutting finger 45 prior to use. In a preferred embodiment, the protective sheath 22 can be made from a plastic such as a low density polyethylene.

Figure 5:
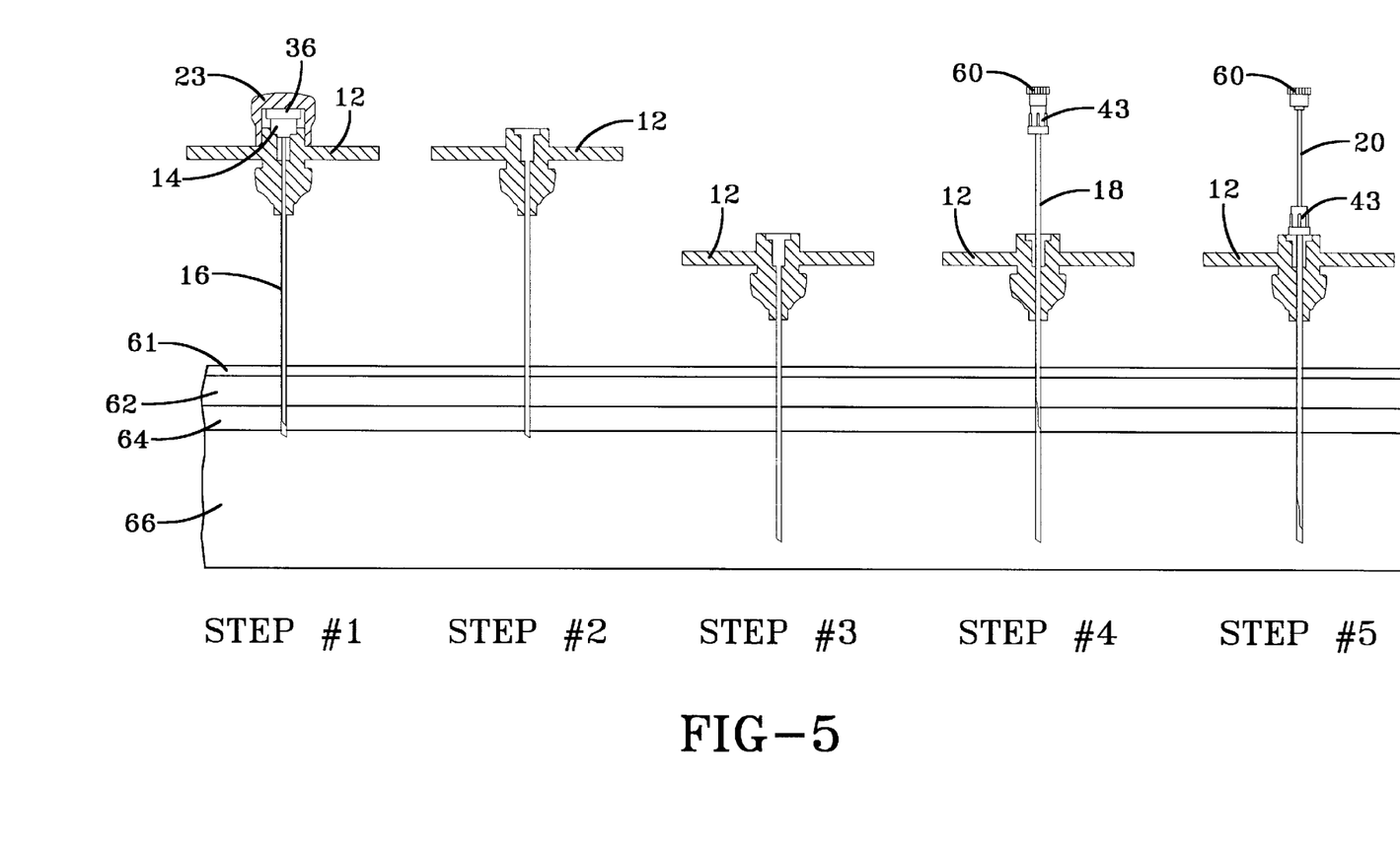
FIG. 5 is a cross-sectional elevational view showing the use of the biopsy device of FIGS. 1 through 3.

Referring now to FIG. 5, use of a bone marrow biopsy device 10 made in accordance with the principles of the present invention is described. The patient comprises outer skin layers 61, a periosteum layer consisting of layers of soft tissue 62, the hard cortex layer of the bone 64, and the medular cavity 66 which contains the bone marrow. In use, the stylet 14 is inserted into the outer cannula 16 and the stylet retaining housing 36 is locked into the handle 12. The health care professional then uses the sharp distal end of the stylet and the beveled distal end of the cannula to penetrate the bone cortex 64. Once the bone cortex 64 has been penetrated and the outer cannula is in the medular cavity 66, the stylet 14 is removed. The outer cannula 16 is then further inserted into the medular cavity 66, thereby trapping bone marrow tissue within the outer cannula 16.

In order to measure the size of the sample, the health care professional can insert the ejector pin 20 into the outer cannula 16. The length of the ejector pin 20 extending outward or proximally from the handle 12 estimates the length of the tissue sample. When an appropriate sample size has been selected, the inner member 18 is extended into the outer cannula 16. The inner member 18 cutting finger 45 slices through a small portion of the tissue sample, with the distal end of the cutting finger 45 extending to within a short distance (p) (seen in FIG. 4) from the distal end of the outer cannula 16. The taper of the distal tip 29 of the outer cannula 16 helps direct the cutting finger 45 inwardly towards the axis of the cannula. The inward extension of the cutting finger 45 helps the cutting finger 45 sever the tissue sample from the tissue.

After the inner member 18 has been fully inserted into the outer cannula 16, the health care professional rotates the inner member 18 by grasping and rotating the hub 43. During this rotation, the cutting finger 45 shears off the specimen while minimizing the amount of crushing effect on the tissue sample. The device 10 is then removed from the patient with the specimen contained within the distal portion of the inner member 18.

Figure 6A:
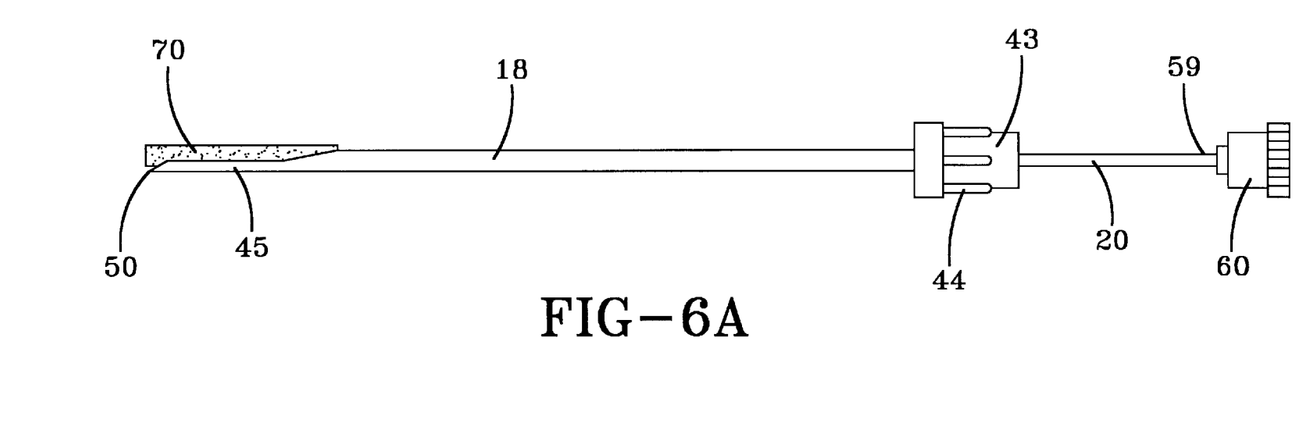
FIG. 6A is a close up view of the inner member and the ejector pin of FIGS. 1 and 2 with a tissue sample in the inner member.
Figure 6B:
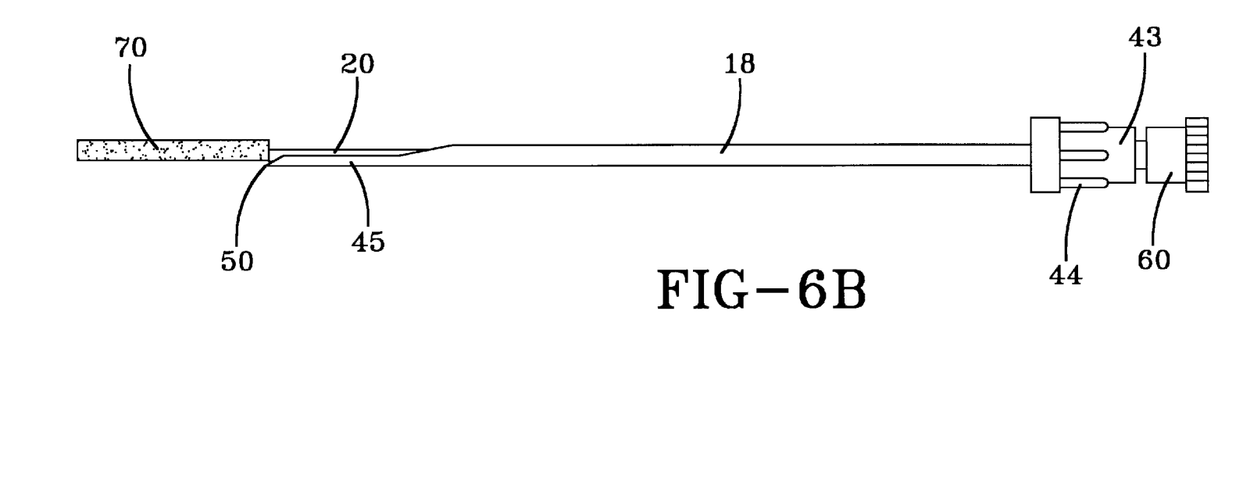
FIG. 6B is a close up view of the inner member and the ejector pin of FIGS. 1 and 2 with the tissue sample removed from the inner member.

Referring now to FIG. 6, the inner member 18, the ejector pin 20, and the tissue sample 70 are seen after removal from the patient. The ejector pin 20 can then be advanced through the inner member 18 to push the specimen out of the inner member 18.

Thus the present invention provides a bone marrow biopsy device that is able to secure a large tissue sample while avoiding increasing the size of the biopsy device thereby minimizing the pain experienced by the patient during such procedure. The bone marrow biopsy device of the present invention further avoids subjecting the tissue sample to undue forces, whether such forces be compression, suction, etc., thus avoiding undue damage to the sample following removal of the tissue from the patient.

Figure 7:
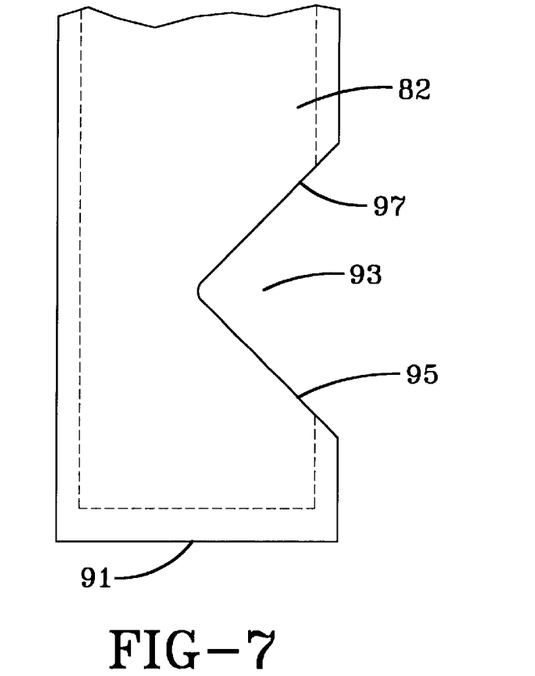
FIG. 7 is a close-up view of the aperture and distal end of the aspiration needle.
Figure 8A:
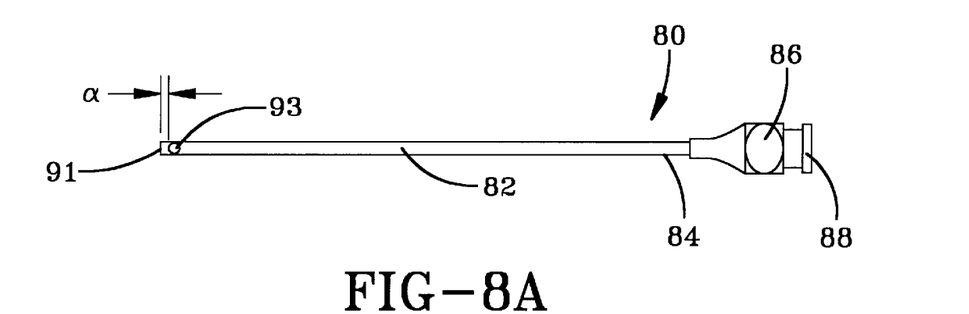
FIG. 8A is a top-view of an aspiration needle made in accordance with the principles of the present invention.
Figure 8B:
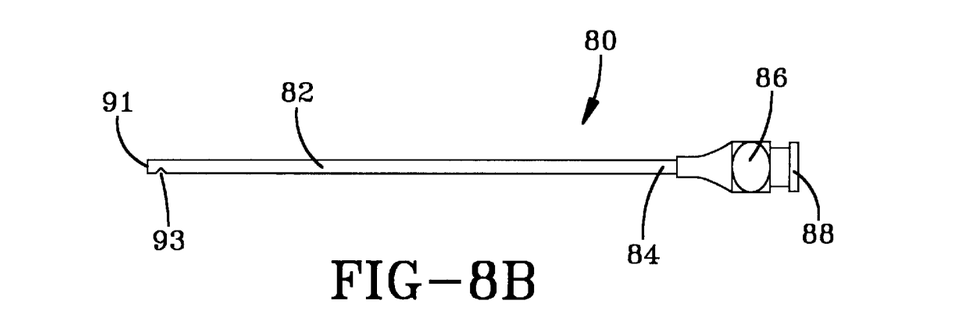
FIG. 8B is a side-view of an aspiration needle made in accordance with the principles of the present invention.

Referring now to FIGS. 7, 8A and 8B, an aspiration needle made in accordance with the principles of the present invention is designated generally by the reference numeral 80. The aspiration needle 80 of the present invention includes a hollow cannula 82. A proximal end 84 of the hollow cannula 82 is secured to a housing 86. The housing 86 defines a connector which is adapted to be mated with a connector contained in a syringe. In a preferred embodiment, the housing 86 defines a female fitting of a luer connector 88 which is adapted to be mated with as male fitting of a luer connector contained in a syringe.

A distal end 91 of the hollow cannula 82 is closed. In a preferred embodiment, the distal end 91 is plugged with, for example, an ultra-violet bond adhesive. A small distance (a) from the closed distal end 91 of the hollow cannula 82, an aperture 93 is defined in the side of the hollow cannula 82. In a preferred embodiment, the aperture 93 is shaped to help direct the suction that is applied to the bone marrow tissue as described in detail below. Other shapes and combinations of apertures that accomplish the desired results are to be considered within the scope of the present invention.

Referring to FIG. 7, detail of the aperture and the distal end of the aspiration needle is seen. In one preferred embodiment, the aperture 93 is shaped with an abrupt distal end 95 and a gradually tapered proximal end 97. Of course, other shapes of the aperture are considered within the scope of the present invention.

The aspiration needle 80 of the present invention is designed to be inserted into an outer cannula 16. When inserted into the outer cannula 16, the aspiration needle forms a seal against the sides of the outer cannula 16. This is an important feature of the present invention as upon the conclusion of the aspiration of the marrow tissue, thrombotic cascading tends to occur thus clotting the aspiration needle 80. By sealing the outer cannula 16 from the aspiration the outer cannula remains free of clotting, thereby allowing a clear biopsy tissue sample to be obtained.

Figure 9:
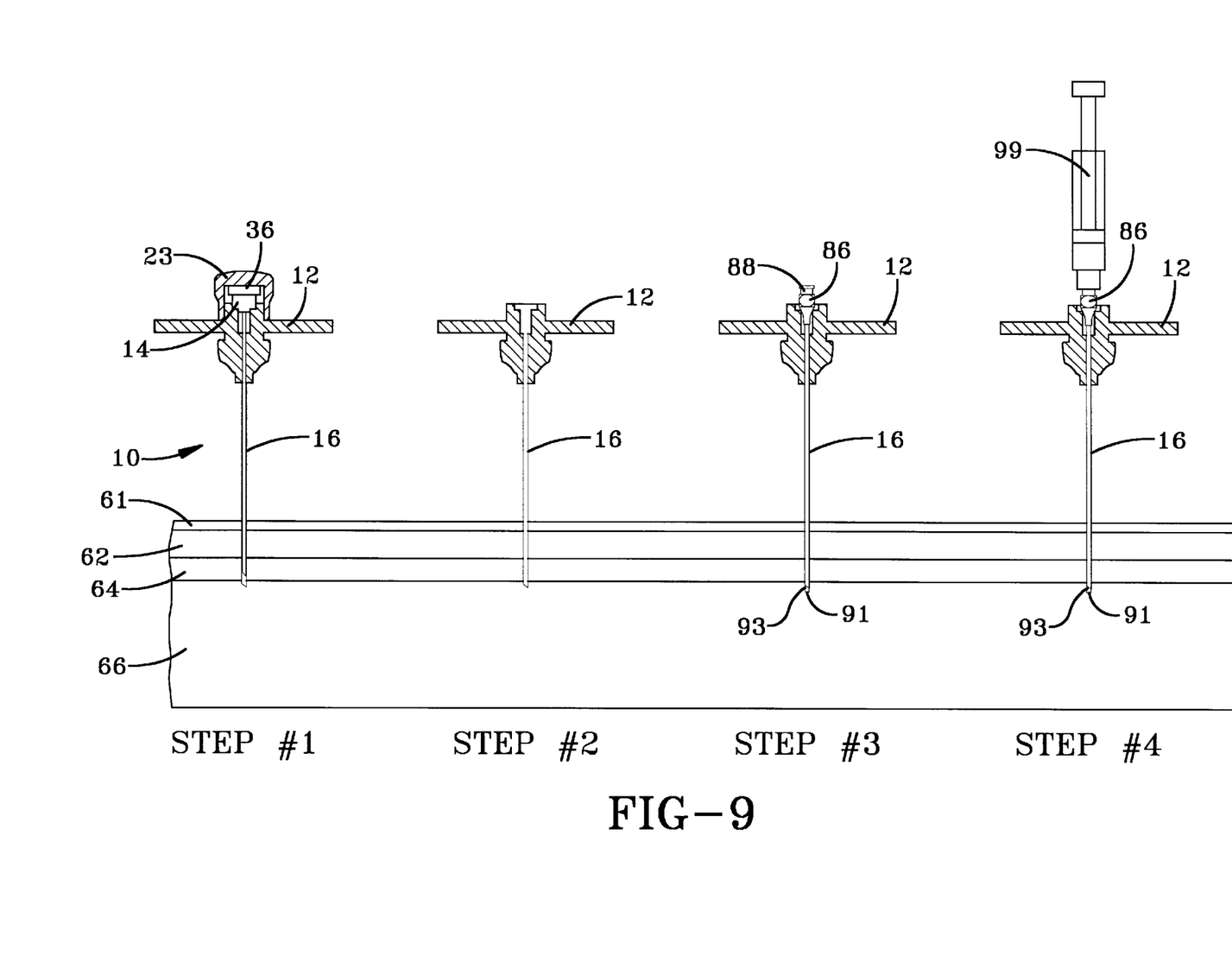
FIG. 9 is a cross-sectional elevational view showing the use of the aspiration needle of FIG. 7.

Referring now to FIG. 9, use of an aspiration needle 80 of the present invention in securing an aspiration sample is described. Initially, a biopsy device is utilized to gain access to the bone medular cavity 66. The stylet 14 is inserted into the outer cannula 16 and the stylet housing 36 is locked into the handle 12. The health care professional then uses the sharp distal end of the stylet ad the beveled distal end of the cannula to penetrate the bone cortex 64. Once the bone cortex 64 has been penetrated and the outer cannula is in the medular cavity 66, the stylet 14 is removed.

Once the stylet 14 and outer cannula 16 have bored through the hard outer cortex layer 64 of the bone, the stylet 14 is removed and the aspiration needle 80 of the present invention is inserted into the outer cannula 16. Subsequently, a syringe 99 is connected to the housing 86 of the aspiration needle 80. As the syringe 99 is retracted, a suction is provided through the hollow cannula 82 to the aperture 93. The suction pulls bone marrow fluid from the marrow tissue into the syringe 99.

Figure 10:
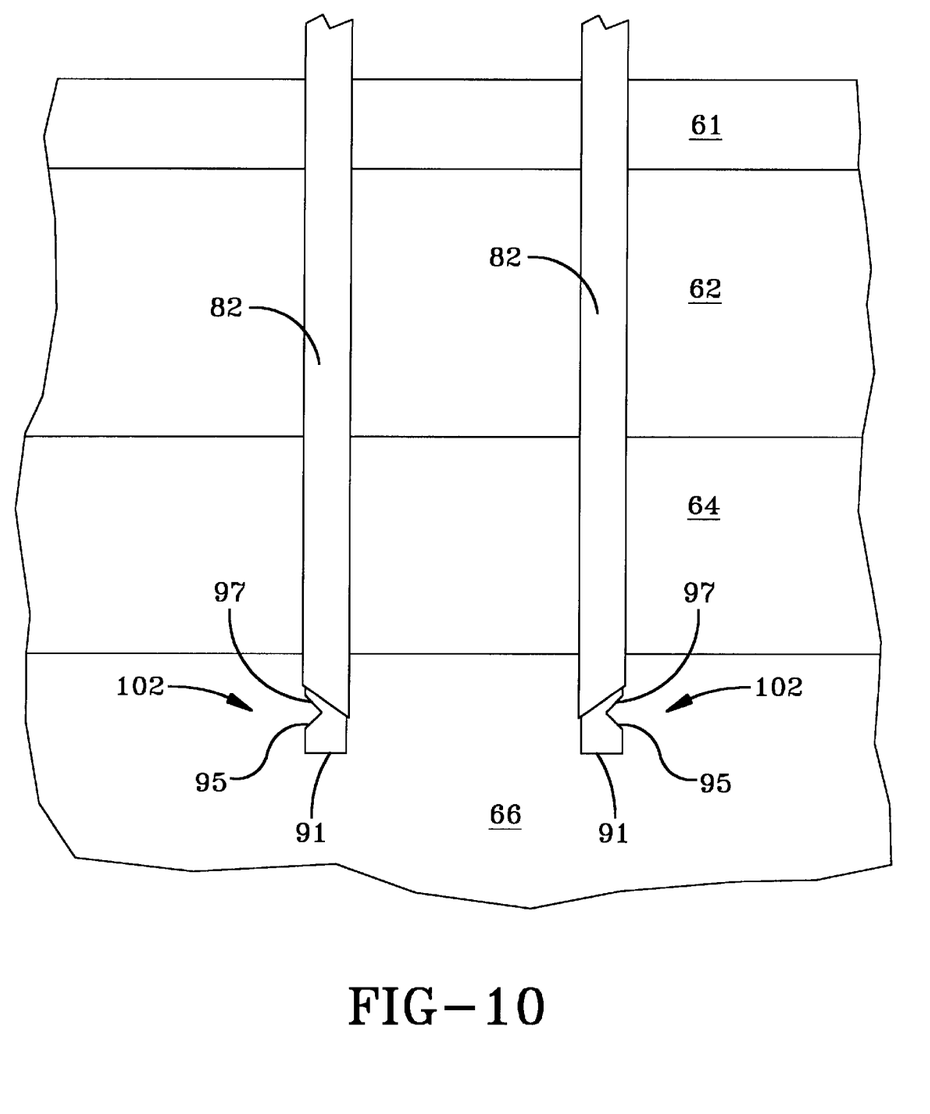
FIG. 10 is a close up view of the aspiration needle of FIGS. 7 and 8 in the medular cavity.

Referring now to FIG. 10, a close-up of the aspiration needle 80 of the present invention is seen positioned in a bone medular cavity 66. The aspiration needle 80 has been inserted into the medular cavity 66 with the aperture 93 extending past the bone cortex 64 into the medular cavity. When suction is applied to the aspiration needle 80 by the syringe 99, the aperture 93 draws marrow fluid from the side of the aspiration needle 80 in a discreet section of the medular cavity. The placement and shape of the aperture 93 directs the suction force in the medular cavity 66 in a direction generally to the side of and upwardly from the aperture 93. The suction force thereby defines a cone shaped aspiration zone 102 generally to the side of and upwardly from the aperture 93. Thus, the bone marrow tissue which is located below the aspiration needle 80 is not adulterated.

In addition, because the aperture 93 directs the suction in this a cone shaped aspiration zone 102, rotation of the aspiration needle 80 exposes new marrow tissue surrounding the aspiration needle 80 to the suction force across the 360° circumference of the hollow cannula 82. Prior art aspiration needles generally do not provide as large of an area from which the marrow fluid can be aspirated.

Upon conclusion of the aspiration, the aspiration needle 80 is removed from the biopsy device 10. The health care professional can then insert the outer cannula 16 deeper into the medular cavity thus trapping bone marrow tissue in the outer cannula 16. Once again, because in the present invention the fluid that has been aspirated from the medular cavity 66 has been drawn from around the sides of the aspiration needle 80 and not below the aspiration needle 80, the tissue sample that is secured by the outer cannula 16 has not been adulterated by the aspiration of the marrow fluid.

Referring now to FIGS. 6A and 6B, the inner member 18, the ejector pin 20, and the tissue sample 70 are seen after removal from the patient. In FIG. 6A the tissue sample 70 remains in the inner member 18. The ejector pin 20 can then be advanced through the inner member 18 to push the specimen out of the inner member 18, as seen in FIG. 6B.

INDUSTRIAL APPLICABILITY

Thus, the present invention meets a long-felt need in the medical community that has not been met by others to provide an aspiration needle that is able to aspirate a sample while minimizing the pain experienced by the patient during such procedure. The present invention further meets a long-felt need in the medical community that has not been met by others to provide an aspiration needle that avoids subjecting the patient to an increased risk of infection during the aspiration. The present invention surprisingly allows for a healthcare professional to both aspirate and obtain a tissue sample from the same access site.

It should be understood that various changes and modifications to the preferred embodiment described herein will be apparent to those skilled in the art. For example, additional shapes of the aspiration needle that likewise direct the suction forced of the aspiration away from the tissue that is sampled can be construed. Such changes and modifications can be made without departing from the spirit and scope of the present invention and without demising its attendant advantages. It is therefore intended that such changes and modifications be covered by the appended claims.

What is claimed is:

1. An aspiration device comprising:
   an outer cannula secured in a handle, the outer cannula defining a distal tip that provides a distal cutting edge;
   a stylet designed to be inserted in the outer cannula, the stylet defining a sharp distal tip;
   a hollow cannula designed to be inserted in the outer cannula; and
   an aperture defined in a side of the hollow cannula.

2. The aspiration device of claim 1 wherein the sharpo distal tip of the stylet is designed to extend to near the distal tip of the outer cannula.

3. The aspiration device of claim 1 further comprising a biopsy device.

4. The aspiration device of claim 3 wherein the biopsy device comprises an inner member designed to be inserted in the outer cannula, the inner member defining a cutting finger.

5. The aspiration device of claim 4 wherein the biopsy device further comprises an ejector pin designed to be inserted into the inner member.

6. The aspiration device of claim 4 wherein the biopsy device further comprises a protective sheath designed to surround the inner member.

7. The aspiration device of claim 1 wherein the hollow cannula is secured in a housing that defines a connector which is adapted to be mated with a connector contained in a syringe.

8. The aspiration device of claim 1 wherein the distal end of the hollow cannula is closed.

9. The aspiration device of claim 8 wherein the distal end of the hollow cannula is plugged with an ultra-violet bond adhesive.

10. A bone marrow aspiration device comprising:
    a housing;
    a hollow cannula secured in the housing and designed to be inserted in an outer cannula; the distal end of the hollow cannula being closed; and
    an aperture defined in a side of the hollow cannula.

11. The aspiration device of claim 9 wherein the housing defines a connector which is adapted to be mated with a connector contained in a syringe.

12. The aspiration device of claim 11 wherein the distal end of the hollow cannula is plugged with an ultra-violet bond adhesive.

13. An aspiration device comprising:

an outer cannula secured in a handle;

a stylet designed to be inserted in the outer cannula; and a hollow cannula designed to be inserted in the outer cannula, the hollow cannula adapted to define an aspiration zone generally to the side of the hollow cannula.

14. The aspiration device of claim 13 wherein an aperture is defined in a side of the hollow cannula.

15. The aspiration device of claim 14 wherein the aperture is shaped to define a cone shaped aspiration zone generally to the side of the hollow cannula.

16. The aspiration device of claim 14 wherein the aperture is shaped to define a cone shaped aspiration zone generally upward from the aperture.

17. The aspiration device of claim 14 wherein the distal end of the hollow cannula is closed.

18. The aspiration device of claim 17 wherein the distal end of the hollow cannula is plugged with an ultra-violet bond adhesive.

19. The aspiration device of claim 16 wherein the outer cannula defines a distal tip that is tapered to provide a distal cutting edge; and the stylet defines a sharp distal tip.

20. The aspiration device of claim 19 wherein the sharp distal tip of the stylet is designed to extend to near the distal tip of the outer cannula.

21. The aspiration device of claim 13 further comprising a biopsy device.

22. The aspiration device of claim 21 wherein the biopsy device further comprises an inner member designed to be inserted in the outer cannula, the inner member defining a cutting finger.

23. The aspiration device of claim 22 wherein the biopsy device further comprises an ejector pin designed to be inserted into the inner member.

24. The aspiration device of claim 22 wherein the biopsy device further comprises a protective sheath designed to surround the inner member.

25. The aspiration device of claim 13 wherein the hollow cannula is secured in housing that defines a connector which is adapted to be mated with a connector contained in a syringe.

26. The aspiration device of claim 16 wherein the distal end of the hollow cannula is plugged with an ultra-violet bond adhesive.

27. A kit for administering an aspiration comprising:

an outer cannula secured in a handle, the outer cannula defining a distal tip that provides a distal cutting edge;

a stylet designed to be inserted in the outer cannula, the stylet defining a sharp distal tip;

a hollow cannula designed to be inserted in the outer cannula; and an aperture defined in a side of the hollow cannula.

28. The kit for administering an aspiration of claim 27 further comprising a biopsy device.

29. The kit for administering an aspiration of claim 28 wherein the biopsy device comprises an inner member designed to be inserted in the outer cannula, the inner member defining a cutting finger.

30. The kit for administering an aspiration of claim 29 wherein the biopsy device comprises an ejector pin designed to be inserted into the inner member.

31. The kit for administering an aspiration of claim 29 wherein the biopsy device comprises a protective sheath designed to curround the inner member.

32. A method for aspirating and sampling bone marrow tissue comprising:

inserting a stylet into an outer cannula;

penetrating the bone cortex with the stylet and the outer cannula to enter the medular cavity;

removing the stylet;

inserting an aspiration needle into the outer cannula;

creating suction through the aspiration needle;

removing the aspiration needle;

further inserting the outer cannula into the medular cavity, thereby trapping bone marrow tissue within the outer cannula; and removing the bone marrow tissue from the patient.

33. The method for aspirating and sampling bone marrow tissue of claim 32 wherein the step of penetrating the bone cortex with the stylet and the outer cannula is achieved by penetrating the bone cortex with a sharp distal end of the stylet and a beveled distal end of the cannula.

34. The method for aspirating and sampling bone marrow tissue of claim 32 further including the step of estimating the length of tissue sample by inserting an ejector pin into the outer cannula after the outer cannula has been further inserted into the medular cavity.

35. The method for aspirating and sampling bone marrow tissue of claim 32 further including the step of extending an inner member into the outer cannula after further inserting the outer cannula, the inner member defining a cutting finger.

36. The method for aspirating and sampling bone marrow tissue of claim 35 further including the step of rotating the inner member to shear off the bone marrow tissue with the cutting finger.

37. The method of aspirating and sampling bone marrow tissue of claim 35 further including the step of extending a distal end of the cutting finger to near a distal end of the outer cannula.

* * * * *